US009359411B2

(12) United States Patent
Huang et al.

(10) Patent No.: US 9,359,411 B2
(45) Date of Patent: Jun. 7, 2016

(54) YEAST EXPRESSED CLASSICAL SWINE FEVER VIRUS GLYCOPROTEIN E2 AND USE THEREOF

(71) Applicant: MAX HSING BIOTECH CO., LTD., New Taipei (TW)

(72) Inventors: Chienjin Huang, Taichung (TW); Maw-Sheng Chien, Taichung (TW); Guang-Jan Lin, Taichung (TW)

(73) Assignee: MAW HSING BIOTECH CO., LTD., New Taipei (TW)

( * ) Notice: Subject to any disclaimer, the term of this patent is extended or adjusted under 35 U.S.C. 154(b) by 0 days.

(21) Appl. No.: 14/106,761

(22) Filed: Dec. 14, 2013

(65) Prior Publication Data

US 2014/0099338 A1    Apr. 10, 2014

Related U.S. Application Data

(63) Continuation-in-part of application No. 12/512,049, filed on Jul. 30, 2009, now abandoned.

(30) Foreign Application Priority Data

Jul. 31, 2008  (TW) ................. 97129117 A (51) Int. Cl.
| | |
|---|---|
| C12Q 1/70 | (2006.01) |
| C12P 1/00 | (2006.01) |
| A61K 39/12 | (2006.01) |
| A61K 39/42 | (2006.01) |
| C07K 14/005 | (2006.01) |
| A61K 39/00 | (2006.01) |

(52) U.S. Cl.
CPC ............... *C07K 14/005* (2013.01); *A61K 39/12* (2013.01); *A61K 2039/552* (2013.01); *A61K 2039/55566* (2013.01); *C12N 2770/24322* (2013.01); *C12N 2770/24334* (2013.01)

(58) Field of Classification Search
None
See application file for complete search history.

(56) References Cited

U.S. PATENT DOCUMENTS 6,180,109 B1 *   1/2001   Moormann et al. ....... 424/204.1

OTHER PUBLICATIONS

Clavijo et al., "Development of a competitive ELISA using a truncated E2 recombinant protein as antigen for detection of antibodies to classical swine fever virus," Research in Veterinary Science 70: 1-7 (2001).*
Huang et al., "Secreted expression of the classical swine fever virus glycoprotein Erns in yeast and application to a sandwich blocking ELISA," Journal of Virological Methods 132: 40-47 (2006).*
Bin et al., "Recombinant Pichia pastoris overexpressing bioactive phytase," Science in China (Series C) vol. 41, No. 3: 330-335 (1998).*

(Continued)

*Primary Examiner* — Benjamin P Blumel
*Assistant Examiner* — M. Franco Salvoza
(74) *Attorney, Agent, or Firm* — Pai Patent Trademark Law Firm; Chao-Chang David Pai (57) ABSTRACT

The present invention provides a recombinant yeast system for expressing the glycoprotein E2 of classical swine fever virus (CSFV), in which the expression level of yE2 is improved by codon optimization and shortening coding region of E2 gene. The truncated E2 subunits are used as major active ingredient in anti-CSFV vaccines and useful diagnostic blocking ELISA kits for CSFV infection with easy manipulation and low cost.

5 Claims, 5 Drawing Sheets

(56) References Cited

OTHER PUBLICATIONS

Chen et al., "Expression and Secretion of Human Bone Morphogenetic Protein-7 in Pichia pastoris," Chinese Journal of Biotechnology, vol. 22, No. 6: 907-912 (2006).*

Bouma et al., "Efficacy and stability of a subunit vaccine based on glycoprotein E2 of classical swine fever virus," Veterinary Microbiology 66: 101-114 (1999).*

Colijn et al., "An improved ELISA for the detection of serum antibodies directed against classical swine fever virus," Veterinary Microbiology: 15-25 (1997).*

Risatti et al., "N-Linked Glycosylation Status of Classical Swine Fever Virus Strain Brescia E2 Glycoprotein Influences Virulence in Swine," Journal of Virology, vol. 81, No. 2: 924-933 (2007).*

Rock et al., "Natural endogenous adjuvants," Springer Semin Immun 26: 231-246 (2005).*

* cited by examiner

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Primer yE2N1F

<400> SEQUENCE: 1
ttatcgatta gactagcctg caagg                                         25

<210> SEQ ID NO 2
<211> LENGTH: 24
<212> TYPE: DNA
<213> ORGANISM: Artificial Sequence
<220> FEATURE:
<223> OTHER INFORMATION: Primer yE2N190F

<400> SEQUENCE: 2
gtatcgatta gactagcctg caag                                          24
```

```
<210> SEQ ID NO 3
<211> LENGTH: 25
<212> TYPE: DNA
<213> ORGANISM: Artificial Sequence
<220> FEATURE:
<223> OTHER INFORMATION: Primer yE2N342R

<400> SEQUENCE: 3
cgctctagaa attctgcgaa gtaat                                    25

<210> SEQ ID NO 4
<211> LENGTH: 25
<212> TYPE: DNA
<213> ORGANISM: Artificial Sequence
<220> FEATURE:
<223> OTHER INFORMATION: Primer yE2N330R

<400> SEQUENCE: 4
cgctctagat ccaggtcaaa ccagt                                    25

<210> SEQ ID NO 5
<211> LENGTH: 25
<212> TYPE: DNA
<213> ORGANISM: Artificial Sequence
<220> FEATURE:
<223> OTHER INFORMATION: Primer yE2N301R

<400> SEQUENCE: 5
cgctctagag tttttgcgta attga                                    25

<210> SEQ ID NO 6
<211> LENGTH: 24
<212> TYPE: DNA
<213> ORGANISM: Artificial Sequence
<220> FEATURE:
<223> OTHER INFORMATION: Primer yE2N190R

<400> SEQUENCE: 6
cggaattctt tcacacatgt ccag                                     24
```

YEAST EXPRESSED CLASSICAL SWINE FEVER VIRUS GLYCOPROTEIN E2 AND USE THEREOF

CROSS-REFERENCE TO RELATED APPLICATION

This application is a continuation-in-part of application Ser. No. 12/512,049 filed Jul. 30, 2009, which claims priority of Taiwan Patent Application No. 97129117, filed on Jul. 31, 2008, the entirety of which is incorporated by reference herein.

FIELD OF THE INVENTION

The present invention relates to a recombinant yeast system for expressing the glycoprotein E2 of classical swine fever virus (CSFV), in which the expression level of the yeast-expressed glycoprotein E2 of CSFV (yE2) is improved by codon optimization and shortening coding region of E2 gene. The truncated E2 subunits are used as major active ingredient in anti-CSFV vaccines and useful diagnostic ELISA kits for CSFV with easy manipulation and low cost.

BACKGROUND OF THE INVENTION

Classical swine fever virus (CSFV) is a virus of the genus *Pestivirus* in the family Flaviviridae (Leyssen et al., 2000, *Clin. Microbiol. Rev.* 13, 67-82). The infection of CSFV in pigs causes clinical symptoms such as fever and bleeding. Because it is highly infectious and lethal, it can cause economic damage to animal husbandry (Vilcek et al., 1996, *Virus Res.* 43, 137-147). The genome of CSFV consists of a (+) RNA of 12.5 kb encoding a giant polyprotein, which is digested into mature viral structural and non-structural proteins by protease of the host cell or the virus (Chamber et al., 1990, *Annu. Rev. Microbiol.* 44, 649-688). The structural proteins of CSFV include nucleocapsid protein C, envelope glycoproteins $E^{rns}$, E1, and E2 (Dong & Chen, 2007, *Vaccine* 25, 205-230). Among these, E2 and $E^{rns}$ have been proved to have the ability to induce neutralizing antibody production in the host (see, for example, Bouma et al., 2000, *Vaccine* 18, 1374-1381; Konig et al., 1995, *J. Virol.* 69, 6479-6486; van Rijn et al., 1993, *J. Gen. Virol.* 74, 2053-2060; and Weiland et al., 1992, *J. Virol.* 66, 3677-3682).

CSFV glycoprotein E2 is the major viral antigen for inducing neutralizing antibody production in pigs. Therefore, E2 is the target protein in the development of CSFV vaccines. Recently, E2 subunit vaccine has been successfully produced by insect cell expression system infected with baculovirus (Hulst et al., 1994, *Virology* 2000, 558-565; Bouma et al., 2000, supra; and van Oers et al., 2001, *J. Biotechnol.* 86, 31-38). E2 subunit vaccine can not only protect pigs against CSFV infection, but may be used to distinguish the immunized pigs from CSFV-infected pigs by detecting anti-$E^{rns}$ and E2 antibodies (de Smit et al., 2000, *Vet. Q.* 22, 182-188; Floegel-Niesmann, 2001, *Vet. Microbiol.* 83, 121-136; and Moormann et al., 2000, *Vet. Microbiol.* 73, 209-219). It is the most important advantage of the marker vaccine. However, the procedure of insect cell expression is very complex, laborious, easy to be contaminated and costly, making large scale production difficult.

Previously, the inventor has successfully produced active $E^{rns}$ protein by yeast *Pichia pastoris* expression system (Huang et al., 2006, *J. Virol. Methods* 132, 40-47). The yeast expression system possesses the characteristics of cultivating at high density and in a cheaper medium, and, especially, can perform the glycosylation modification as in eukaryotes to produce in large quantity the desired glycoprotein at high efficiency and low cost. Accordingly, the aim of the present invention is to prepare recombinant glycoprotein E2 of classical swine fever virus by using yeast (for example, *Pichia pastoris*) expression system.

The advantages of this eukaryotic expression system include simple manipulation, easy purification, and cost (Cereghino and Cregg, *FEMS Microbiol Rev* 24: 45-66, 2000). However, several genetic and physiological factors determine the productivity of a recombinant system (Hohenblum et al., *J Biotechnol* 102: 281-290, 2003). Synonymous codon usage bias differences, one major factor among others, has a significant impact on heterologous gene expression (Sinclair and Choy, *Protein Expres Purif* 1: 96-105, 2002; Su et al., *Vet Microbiol* 124: 256-263, 2007). To improve the expression yield of yE2, the first codon CGG (Arg) of E2 gene which is the least use in *P. pastoris*, was optimized to the most favorite codon AGA, and several truncated mutants were also constructed and evaluated for their immunogenicities in pigs.

SUMMARY OF THE INVENTION

One of the objects of the invention is to provide a process for producing truncated yeast-expressed E2 subunits of classical swine fever virus (yE2) by using a recombinant yeast expression system. The process comprises: cloning a defined coding region of C-terminus truncated E2 with the first arginine codon changed to AGA into the yeast expression vector pGAPZαC (Invitrogen) to construct a recombinant expression plasmid; transforming the obtained recombinant expression plasmid into *Pichia pastoris* host cells; cultivating the transformant cells under an appropriative condition for the expression and secretion of the truncated yE2 glycoprotein into culture medium; and isolating and purifying the recombinant truncated yE2 glycoprotein from the supernatant of culture medium.

In some embodiments of the present invention, the recombinant truncated yE2 includes the yE2 subunits E2N330, E2N301, and E2N190, which have the a.a. residues 1-330, 1-301, and 1-190 of yE2 glycoprotein, respectively.

Another object of the invention is to provide a recombinant truncated yE2 glycoprotein of classical swine fever virus produced in yeast expression system. The recombinant truncated yE2 proteins N330 is characterized to be able to form a homodimer and exhibits glycosylation conformation and correct antigenicity. The expression level and yield of the truncated yE2 proteins are remarkably increased.

Yet another object of the invention is to provide a subunit vaccine for protecting pigs from the infection of CSFV, which comprises a truncated yE2 glycoprotein of classical swine fever virus produced according to the present invention, and a veterinarily acceptable adjuvant. In an embodiment of the invention, the recombinant yE2 subunit is selected from the group consisted of E2N330, E2N301, and E2N190, which have the a.a. residues 1-330, 1-301, and 1-190 of yE2 glycoprotein, respectively.

Yet another object of the invention is to provide a blocking ELISA kit for detecting antibody against E2, comprising the recombinant truncated yE2 subunit of the present invention as a coating material, and a monoclonal antibody against E2.

The other features of the invention will be described in the detailed disclosure of following embodiments.

DETAILED DESCRIPTION OF THE INVENTION

The preferred embodiments of the invention will be described as follows. These examples are given for illustration of the invention and are not intended to be limiting. It will be apparent to those skilled in the art that many modifications may be practiced without departing from the purpose and interest of this invention.

EXAMPLES

Example 1

Expression of Truncated CSFV E2 Protein Variants in *Pichia pastoris*

The defined coding region corresponding to the a.a. residues 1-342, 1-330, 1-301, and 1-190 of E2 was amplified by polymerase chain reaction (PCR) using the specific primer pair with the first arginine codon changed to AGA, respectively (as listed in Table 1). The PCR reaction was carried out as described previously (Lin et al., *Vet Microbio*l 139: 369-374, 2009). The amplified E2 gene fragment was gel-purified and then treated with appropriate restriction enzymes for cloning into the yeast expression vector pGAPZαC (Invitrogen) to construct the expression plasmid pGAPZαC/E2N342, pGAPZαC/E2N330, pGAPZαC/E2N301, and pGAPZαC/E2N 190, respectively. The accuracy of the ORF of E2 coding sequences was confirmed by DNA sequencing.

TABLE 1

Sequences of oligonucleotides used for cloning the defined coding region of CSFV E2 protein.

| Oligo-nucleo-tide | Sequence in 5'-3' direction[a] | SEQ ID NO: | Restriction site |
|---|---|---|---|
| yE2N1F | TTATCGATTAGACTAGCCTGCAAGG | 1 | ClaI |
| yE2N190F | GTATCGATTAGACTAGCCTGCAAG | 2 | ClaI |

TABLE 1-continued

Sequences of oligonucleotides used for cloning the defined coding region of CSFV E2 protein.

| Oligo-nucleo-tide | Sequence in 5'-3' direction[a] | SEQ ID NO: | Restriction site |
|---|---|---|---|
| yE2N342R | CGCTCTAGAAATTCTGCGAAGTAAT | 3 | XbaI |
| yE2N330R | CGCTCTAGATCCAGGTCAAACCAGT | 4 | XbaI |
| yE2N301R | CGCTCTAGAGTTTTTGCGTAATTGA | 5 | XbaI |
| yE2N190R | CGGAATTCTTTCACACATGTCCAG | 6 | EcoRI |

[a]The sequences recognized by the restriction enzyme are boxed and the first codon of E2 gene was optimized to AGA which is underlined.

In Table 1, the SEQ ID NOs (in the sequence listing concurrently submitted with the application) corresponding to the oligonucleotides are also indicated.

Recombinant expression plasmids were transformed respectively into *Pichia pastoris* SMD 1168 competent cells using *Pichia* EASYCOMP Kit (Invitrogen) according to the manufacturer's manual. Transformed cells were then plated onto yeast extract peptone dextrose (YPD; 1% yeast extract, 2% peptone, 2% glucose) agar containing 100 μg/ml Zeocin (Invitrogen) and incubated at 30° C. for 2-3 days until single colonies were formed. A single colony of recombinant yeast was inoculated in 5 ml YPD medium and incubated at 30° C. in a shaking incubator (250 rpm) overnight. Then 0.1 ml of the overnight culture was transferred to 50 ml fresh YPD medium in a 250 ml baffled flask and was continuously incubated for 4 days. The supernatants were clarified by centrifugation (20 min, 12,000×g, 4° C) and secreted protein was concentrated by ultrafiltration using Centricon YM-10 or 30 (Millipore) filter devices, followed by dialysis against phosphate-buffered saline (PBS). The protein concentration was determined by the use of a Bradford protein assay kit (Bio-Rad).

Figure 1:
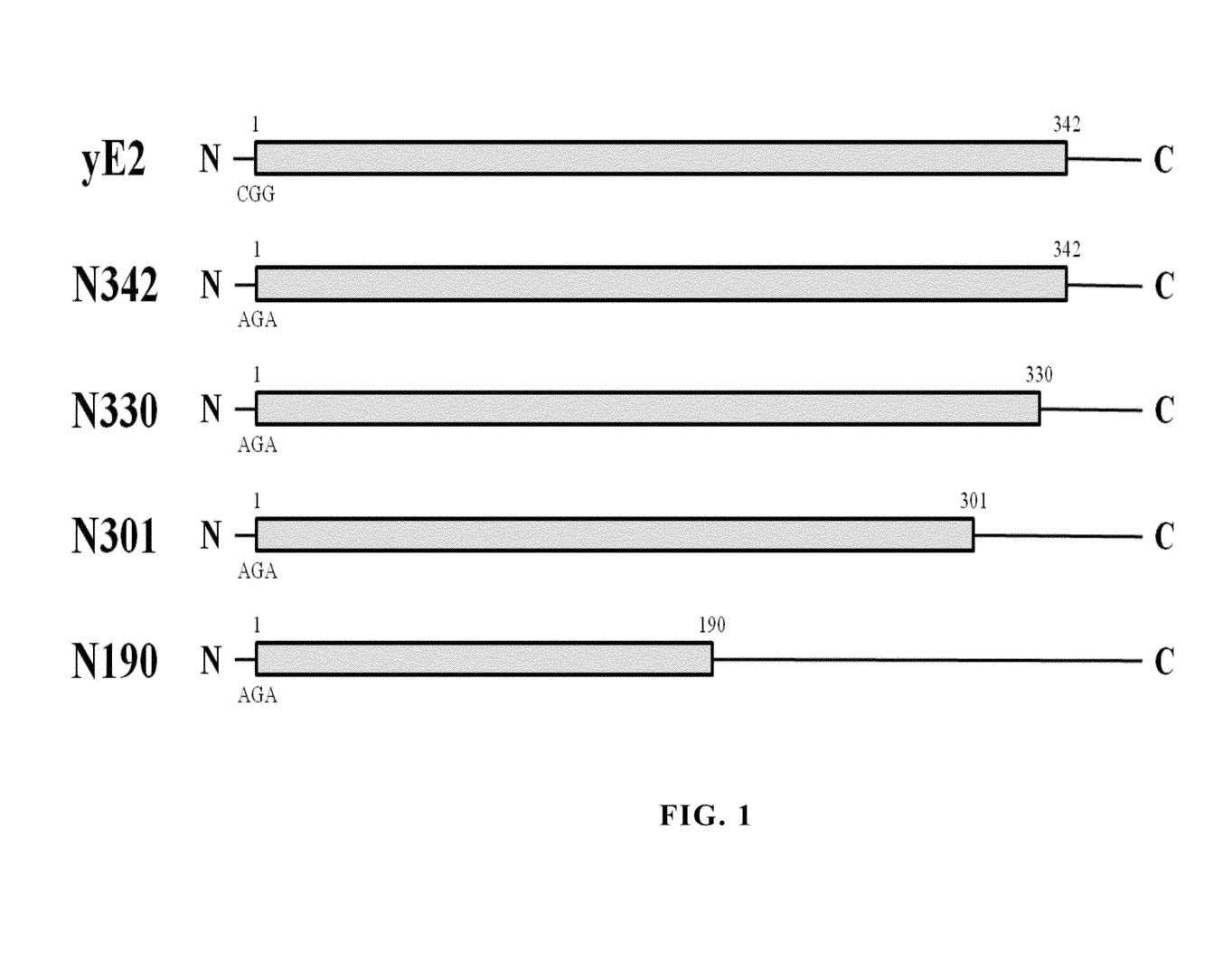
FIG. 1 shows the schematic diagram of the expressed coding regions of E2 recombinant subunits. The bars represent expressed coding sequences. The amino acid residue numbers at both termini and the first codon for arginine are indicated.
Figure 2:
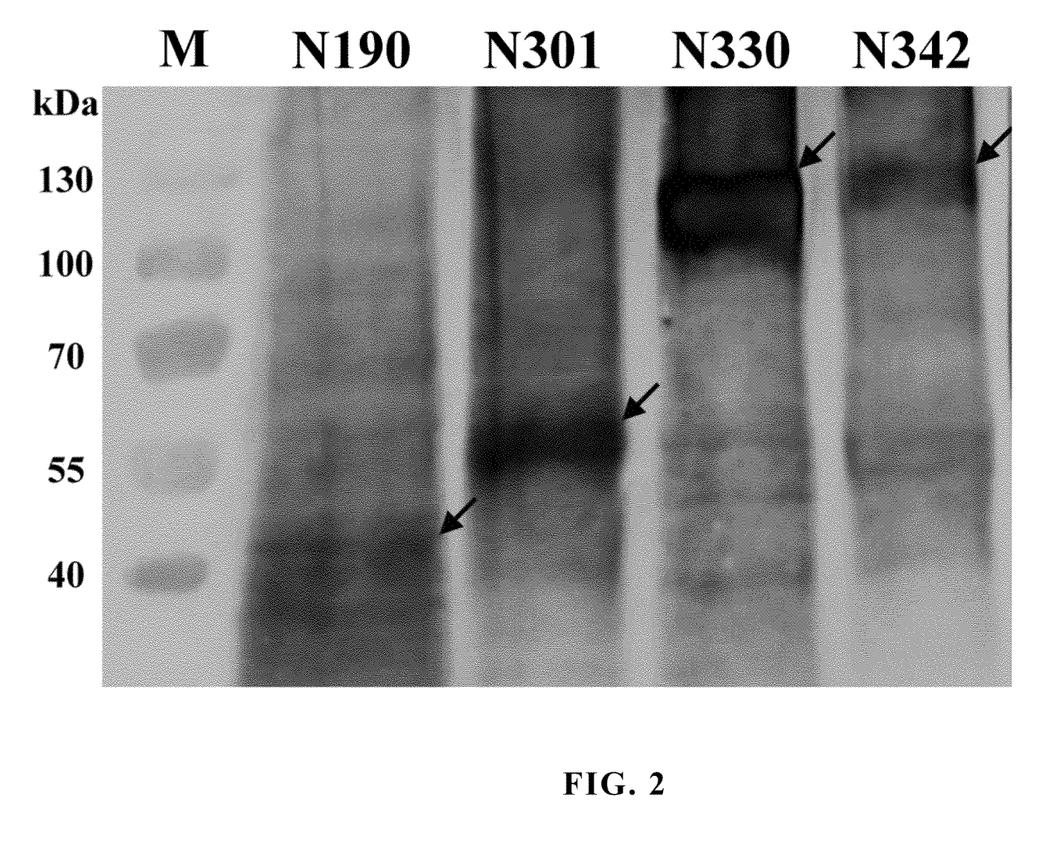
FIG. 2 shows Western blot analysis result of the recombinant truncated E2 proteins. Expressed E2 proteins were separated by 12% SDS-PAGE in the absence of β-mercaptoethanol followed by Western blot analysis with monoclonal antibody specific to E2. The expected E2 protein is indicated by an arrow.
Figure 3:
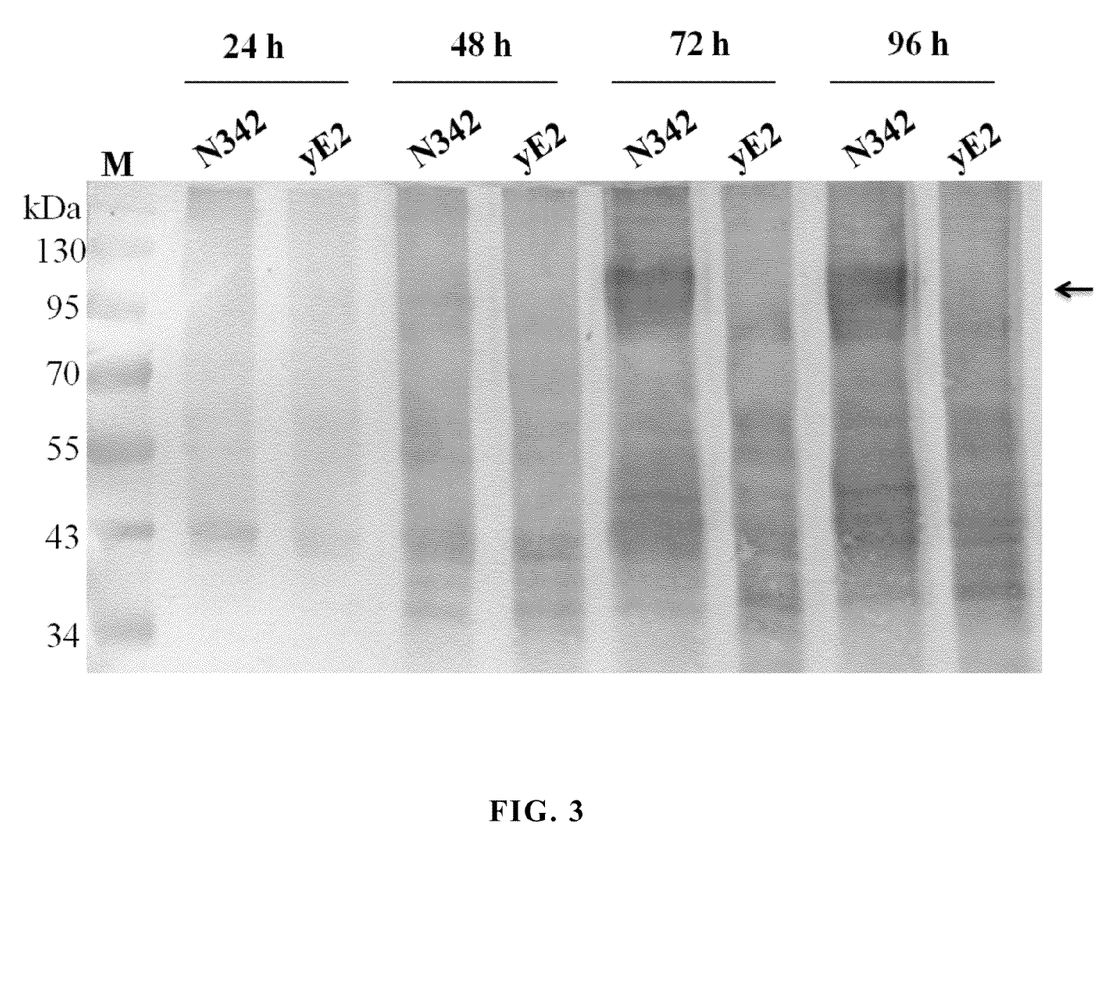
FIG. 3 shows comparison of the expression levels between two full-length E2 recombinant proteins. The culture supernatants of E2N342 and yE2 were harvested at 24 h, 48 h, 72 h, and 96 h, respectively. The expressed E2 proteins were separated by 12% SDS-PAGE in the absence of β-mercaptoethanol followed by Western blot analysis with the monoclonal antibody specific to E2.

Schematic diagrams of N342, E2N330, E2N301, and E2N190 are shown in FIG. 1. Expressed N342 and truncated subunits were analyzed by Western blotting analysis with the MAb specific to E2 (FIGS. 2). N342 and N330 could form homodimer while N301 and N190 were predominantly monomers. The expression level of N342 was further compared with yE2 at 24 h-interval for 4 days. Remarkable increases of yield in N342 were revealed during the entire expression course (FIG. 3).

Few codons of the CSFV E2 gene are seldom used in yeast, though it was successfully expressed in our previous study (Lin et al., *Vet Microbiol* 139: 369-374, 2009). To improve the yield of yE2, the first codon (CGG) of E2 gene was optimized to AGA, and shorter coding regions were also constructed. The expression level of yE2 was increased remarkably after the first codon was changed (FIG. 3), while no obvious difference was observed between various truncated yE2 subunits (FIG. 2). Successful translation indicated that passing with high frequency certainly circumvents the bottleneck of *P. pastoris* expression system.

Example 2

Immunization of Pigs

The yeast-expressed E2 (yE2), which is capable of inducing a complete protective immune response and preventing horizontal transmission of CSFV, appears to be a potential subunit marker vaccine (Lin et al., *Vaccine* 30: 2336-2341, 2012). The immunogenicity of each truncated yE2 recombinant proteins were evaluated by immunization of pigs. Fifteen 6-week-old specific-pathogen-free (SPF) piglets were randomly allotted to 5 groups. Each piglet was immunized intramuscularly into the neck region with one dose of vaccine twice at 3-week intervals. Each dose of vaccine contained 300 µg of each expressed E2 variants including the N342, N330, N301, and N190 groups or normal saline (the control group) in a 1:1 water-in-oil emulsion with the adjuvant ISA563 (SEPPIC).

Figure 4:
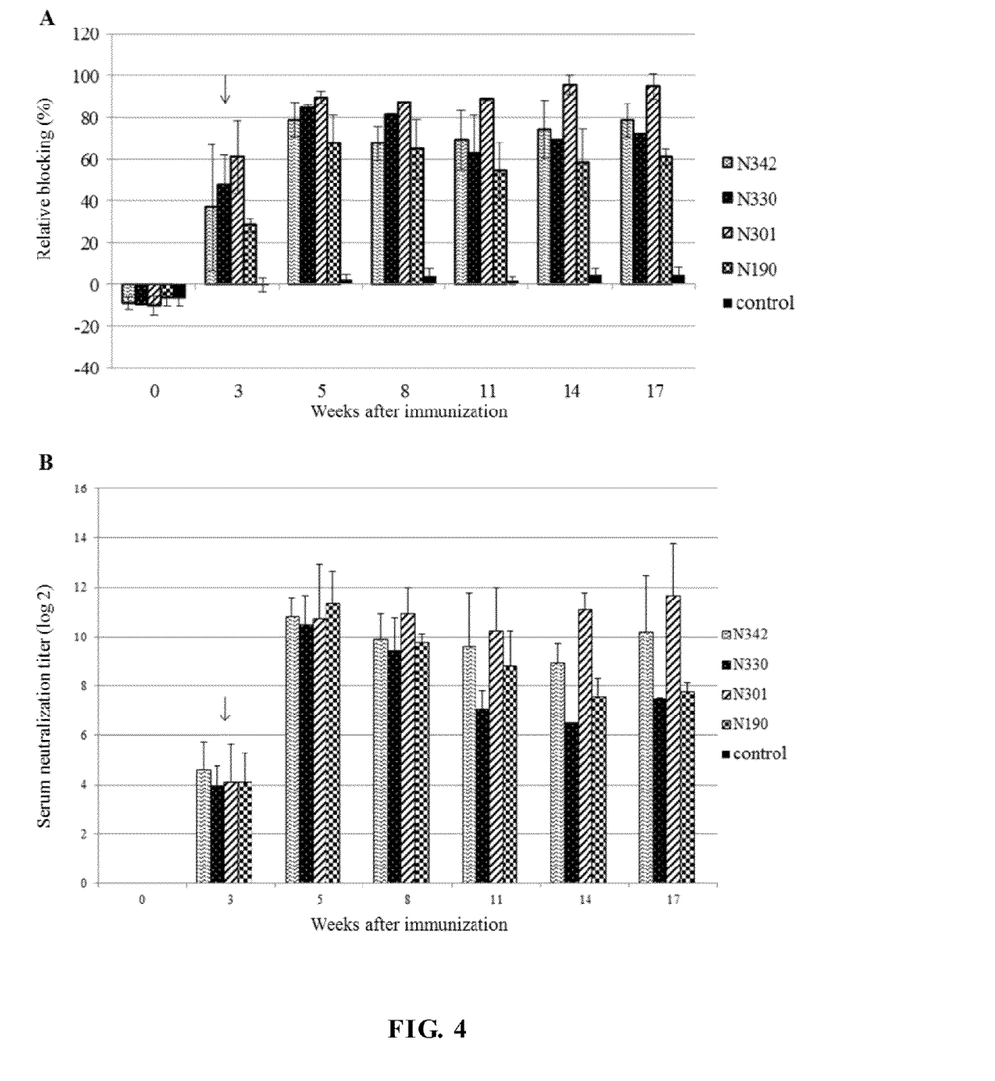
FIG. 4 shows the time course of ELISA antibody development (A) and neutralizing antibody (B) of variant E2 recombinant proteins immunized pigs after vaccination. All of the pigs received a booster immunization (↓) at 3 weeks post-immunization.

All recombinant E2-immunized pigs showed strong antibody responses and seroconverted to CSFV-E2-specific antibody after booster vaccination as determined by a commercial E2-blocking ELISA test, while no antibody was detected in the serum of control pigs (as showed in FIG. 4A). All the N342, N330, N301, and N190 groups could mount anamnestic responses after booster vaccination with average neutralizing antibody titers of 1:1789, 1:1448, 1:1708, and 1:2572, respectively, and sustained for at least 12 weeks with titers above the protective titer of 1:32 (FIG. 4B). It showed that those recombinant yE2 subunits represent a potential subunit E2 marker vaccine candidate with advantages of easy manipulation and low cost.

Example 3

Development of a Blocking ELISA for Detecting Antibody Aagainst E2

In the present invention, a MAb specific to E2 (1B6)- and yE2 subunit (N330)-based blocking ELISA was established. A stable hybridoma secreting antibody reacting specifically with CSFV-infected cells in indirect immunofluorescence (IIF) assay was selected and cloned. This MAb, 1B6, was determined to be the type of IgG1 subclass (data not shown), and also demonstrated neutralizing antibody activity to all three different genotypes of CSFV infection in the neutralization assay. The MAb was purified by Protein A/G affinity column (Pierce) followed by conjugating with HRP using SURELINK Activated HRP (KPL) to generate the HRP-anti-E2 (1B6) conjugate.

Figure 5:
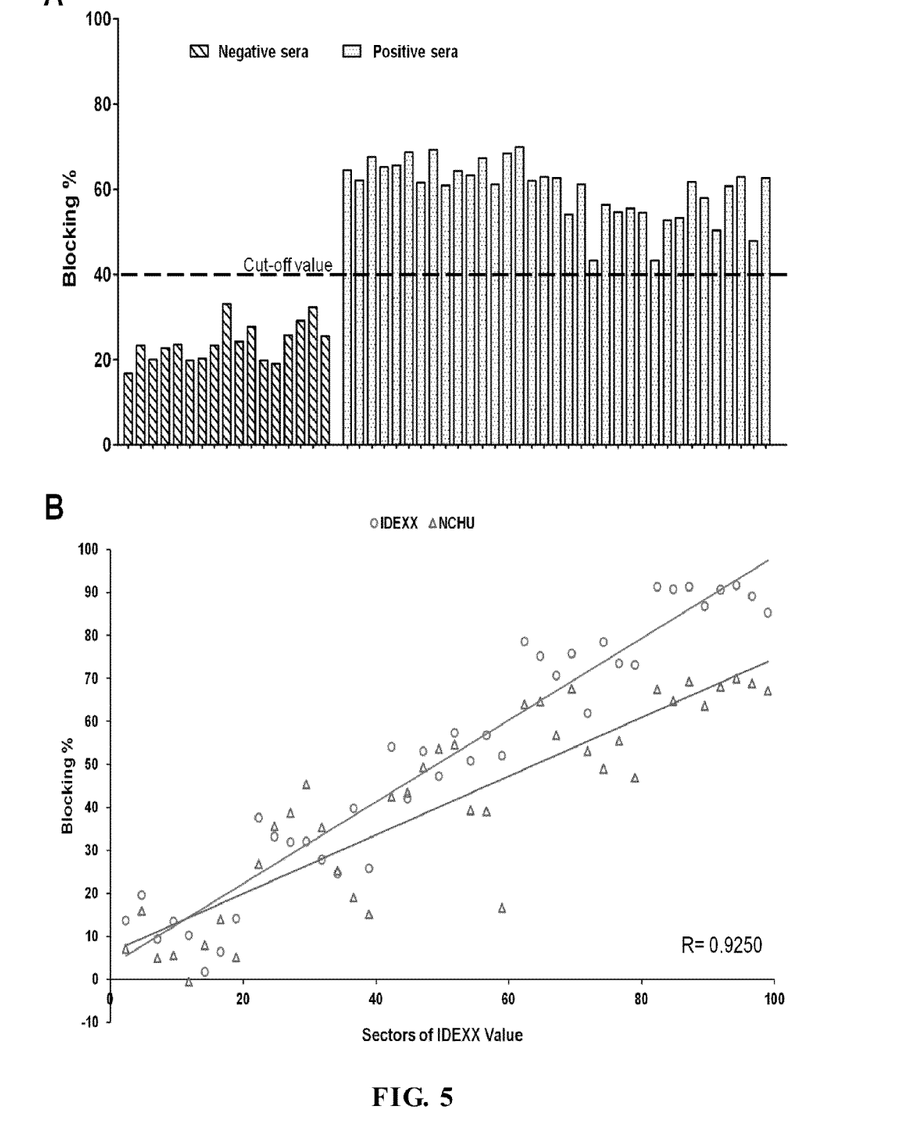
FIG. 5 shows the reactivities of swine sera to yE2 in the blocking ELISA (A) and the comparison to a commercial ELISA kit (B).

ELISA plates (Corning) were coated at 4° C. overnight with 50 µl of 1 µg/ml purified N330 in coating buffer (carbonate buffer, pH 9.6). The plate was then thoroughly washed with PBS containing 0.05% Tween-20 (PBST) and blocked with PBS containing 3% bovine serum albumin (BSA) 37° C. for 1 h. After washing, each well received 50 µl of 2-fold dilution of tested swine serum in dilution buffer (PBS containing 1% BSA) and was incubated at 37° C. for 1 h. Subsequently, the plate was washed with PBST thoroughly and each well received 50 µl of 500-fold dilution of HRP-MAb anti-E2 (1B6) conjugate in dilution buffer at 37° C. for 45 min. Finally, the plate was washed with PBST three times and PBS twice. Then, 100 µl of freshly prepared chromogen/substrate solution (ABTS single solution, Zymed) was added into each well and the plate was incubated at room temperature for 15 min. The optical density of each well was read at 405 nm using a microplate reader (MRXII, Dynex). Each sample was analyzed in duplicate, and the mean OD value of each tested sample (=$OD_{TEST}$) and that of the negative control (=$OD_{NEG}$) were calculated. The inhibition percentage of each sample was calculated according to the following formula: Blocking %=[($OD_{NEG}$−$OD_{TEST}$)÷$OD_{NEG}$]×100. The results expressed as blocking % are shown in FIG. 5A.

The blocking percentages of 17 negative sera were ranged 16.8% to 33.1% with average of 23.9%, while in 35 positive sera were ranged 43.3% to 69.9% with average of 60%. When the blocking percentage cut-off value was set at 40%, among 17 negative sera were determined as negative and resulted in a specificity of 100%, and all the positive sera were positive with the corresponding sensitivities of 100%. When the cut-off value was set more restricted at 45% and 50%, the sensitivities were decreased slightly to 94.3% (33/35) and 91.4% (32/35), respectively. A correlation coefficient between our established blocking ELISA (NCHU) and the commercial ELISA kit (IDEXX) was determined, and a regression line was plotted between blocking percentages of the corresponding serum sample using Microsoft Excel as shown in FIG. 5B.

The assay in blocking ELISA of the invention demonstrates a high sensitivity and specificity, and high correlation with a commercial CSFV E2 blocking ELISA kit (IDEXX), which may offer a useful and inexpensive method for routine diagnosis of swine antibody to E2.

What is claimed is:

1. A subunit vaccine for protecting pigs against classical swine fever virus (CSFV) infection, which comprises a recombinant truncated yE2 subunit and a veterinarily acceptable adjuvant, wherein the recombinant truncated yE2 subunit is yE2 subunit E2N330 having the amino acid residues 1-330 of yE2 glycoprotein produced by a method comprising the steps of: (a) cloning a coding region for amino acid residues 1-330 of E2 glycoprotein with the first arginine codon changed to AGA into the yeast expression vector pGAPZαC to construct a recombinant expression plasmid; (b) transforming the recombinant expression plasmid obtained in step (a) into Pichia pastoris host cells to obtain transformant cells; (c) cultivating the transformant cells under a condition for expression and secretion of truncated yE2 glycoprotein into a culture medium; and (d) isolating and purifying the recombinant truncated yE2 glycoprotein from the supernatant of the culture medium of step (c).

2. A subunit vaccine for protecting pigs against classical swine fever virus (CSFV) infection, which comprises a recombinant truncated yE2 subunit and a veterinarily acceptable adjuvant, wherein the recombinant truncated yE2 subunit is yE2 subunit E2N301 having the amino acid residues 1-301 of yE2 glycoprotein produced by a method comprising the steps of: (a) cloning a coding region for amino acid residues 1-301 of E2 glycoprotein with the first arginine codon changed to AGA into the yeast expression vector pGAPZαC to construct a recombinant expression plasmid; (b) transforming the recombinant expression plasmid obtained in step (a) into Pichia pastoris host cells to obtain transformant cells; (c) cultivating the transformant cells under a condition for expression and secretion of truncated yE2 glycoprotein into a culture medium; and (d) isolating and purifying the recombinant truncated yE2 glycoprotein from the supernatant of the culture medium of step (c).

3. A subunit vaccine for protecting pigs against classical swine fever virus (CSFV) infection, which comprises a recombinant truncated yE2 subunit and a veterinarily acceptable adjuvant, wherein the recombinant truncated yE2 subunit is yE2 subunit E2N190 having the amino acid residues 1-190 of yE2 glycoprotein produced by a method comprising the steps of: (a) cloning a coding region for amino acid residues 1-190 of E2 glycoprotein with the first arginine codon changed to AGA into the yeast expression vector pGAPZαC to construct a recombinant expression plasmid; (b) transforming the recombinant expression plasmid obtained in step (a) into Pichia pastoris host cells to obtain transformant cells; (c) cultivating the transformant cells under a condition for expression and secretion of truncated yE2 glycoprotein into a culture medium; and (d) isolating and purifying the recombinant truncated yE2 glycoprotein from the supernatant of the culture medium of step (c).

4. A blocking ELISA kit for detecting antibody against E2, comprising the recombinant truncated yE2 subunit E2N330 having the amino acid residues 1-330 of yE2 glycoprotein as a coating material, and a monoclonal antibody against E2.

5. The blocking ELISA kit of claim 4, wherein the monoclonal antibody is specific to E2 glycoprotein of classical swine fever virus and the truncated yE2 subunit.

* * * * *